United States Patent
Fink et al.

(10) Patent No.: US 6,784,440 B2
(45) Date of Patent: Aug. 31, 2004

(54) FOOD SANITIZING CABINET

(75) Inventors: Ronald G. Fink, Jupiter, FL (US); Walter Ellis, Jupiter, FL (US); Charles Bearsall, Stuart, FL (US)

(73) Assignee: BOC, Inc., Murray Hill, NJ (US)

( * ) Notice: Subject to any disclaimer, the term of this patent is extended or adjusted under 35 U.S.C. 154(b) by 0 days.

(21) Appl. No.: 10/206,498

(22) Filed: Jul. 26, 2002

(65) Prior Publication Data

US 2004/0016887 A1 Jan. 29, 2004

(51) Int. Cl.$^7$ ............................................... A21D 6/00
(52) U.S. Cl. .................. 250/435; 250/428; 250/432 R; 250/434; 250/436; 250/438
(58) Field of Search ................. 250/428, 429, 250/430, 431, 432 R, 433, 434, 435, 436, 437, 438, 432; 422/24

(56) References Cited

U.S. PATENT DOCUMENTS

| | | | |
|---|---|---|---|
| 4,028,246 A | * 6/1977 | Lund et al. .................... 422/24 |
| 4,094,237 A | 6/1978 | Riordan ........................ 99/451 |
| 4,323,437 A | 4/1982 | Mucenieks ................... 204/98 |
| 4,400,270 A | 8/1983 | Hillman ....................... 210/103 |
| 4,427,636 A | 1/1984 | Obenshain ............. 422/186.07 |
| 4,469,951 A | 9/1984 | Coco et al. .............. 250/494.1 |
| 4,482,809 A | 11/1984 | Maarschalkerweerd ..... 250/436 |
| 4,534,282 A | 8/1985 | Marinoza ..................... 99/451 |
| 4,536,332 A | 8/1985 | Davis et al. ............... 260/97.6 |
| 4,547,197 A | 10/1985 | Winkler ..................... 23/302 T |
| 4,621,195 A | 11/1986 | Larsson ...................... 250/438 |
| 4,661,264 A | 4/1987 | Goudy, Jr. .................. 210/748 |
| 4,694,179 A | 9/1987 | Lew et al. .................... 250/431 |
| 4,766,321 A | 8/1988 | Lew et al. .................... 250/431 |
| 4,798,702 A | 1/1989 | Tucker ........................ 422/24 |
| 4,872,980 A | 10/1989 | Maarschalkerweerd ..... 210/243 |
| 4,899,056 A | 2/1990 | Ellner ......................... 250/431 |
| 4,899,057 A | 2/1990 | Koji ............................ 250/436 |
| 4,922,114 A | 5/1990 | Boehme ...................... 250/436 |
| 4,968,489 A | 11/1990 | Peterson .................. 422/186.3 |
| 4,968,891 A | 11/1990 | Jhawar et al. .............. 250/438 |
| 4,971,687 A | 11/1990 | Anderson ..................... 210/85 |
| 5,006,244 A | 4/1991 | Maarschalkerweerd ..... 210/243 |
| 5,035,784 A | 7/1991 | Anderson et al. ....... 204/158.14 |
| 5,037,618 A | 8/1991 | Hager .................... 422/186.03 |
| 5,114,670 A | 5/1992 | Duffey ......................... 422/24 |
| 5,141,636 A | 8/1992 | Flanagan et al. ........... 210/209 |
| 5,144,146 A | 9/1992 | Wekhof ..................... 250/492.1 |
| 5,145,515 A | 9/1992 | Gallup et al. ................. 75/712 |
| 5,150,705 A | 9/1992 | Stinson ...................... 128/396 |
| 5,166,527 A | 11/1992 | Solymar ..................... 250/436 |
| 5,186,907 A | 2/1993 | Yanagi et al. ............ 422/186.3 |
| 5,200,156 A | 4/1993 | Wedekamp .............. 422/186.3 |
| 5,207,921 A | 5/1993 | Vincent ...................... 210/704 |
| 5,208,461 A | 5/1993 | Tipton ........................ 250/436 |
| 5,230,792 A | 7/1993 | Sauska et al. ................ 210/97 |
| 5,266,215 A | 11/1993 | Engelhard ................... 210/748 |
| 5,288,461 A | 2/1994 | Gray ........................... 422/24 |
| 5,290,439 A | 3/1994 | Buchwald ................. 210/198.1 |

(List continued on next page.)

*Primary Examiner*—John R. Lee
*Assistant Examiner*—James P. Hughes
(74) *Attorney, Agent, or Firm*—Joshua L. Cohen

(57) ABSTRACT

A compact, efficient, easy-to-maintain enclosable cabinet for sanitizing a liquid flowing along a cascade within a cabinet body, having a cabinet body, a plurality of troughs directing the liquid along a predetermined path including a cascade within the cabinet body and one or more sanitizing radiation sources for subjecting the liquid to a sanitizing radiation for a predetermined time while flowing along the predetermined path, whereby the liquid is subject to sufficient sanitizing radiation for a predetermined level of sanitization. The sanitizing radiation sources are assemblies having a UV light source, a UV light shield located between the UV light source and the liquid and a rigid internal reflector shield located between the UV light source and the UV light shield.

28 Claims, 5 Drawing Sheets

U.S. PATENT DOCUMENTS

| | | | |
|---|---|---|---|
| 5,308,505 A | 5/1994 | Titus et al. | 210/745 |
| 5,320,749 A | 6/1994 | Mullen | 210/199 |
| 5,352,359 A | 10/1994 | Nagai et al. | 210/192 |
| 5,366,705 A | 11/1994 | Reidy | 422/243 |
| 5,368,826 A | 11/1994 | Weltz et al. | 422/243 |
| 5,393,419 A | 2/1995 | Tiede et al. | 210/192 |
| 5,401,394 A | 3/1995 | Markham | 210/85 |
| 5,413,768 A | 5/1995 | Stanley, Jr. | 422/186.3 |
| 5,418,370 A | 5/1995 | Maarschalkerweerd | 250/431 |
| 5,422,487 A | 6/1995 | Sauska et al. | 250/436 |
| 5,440,131 A | 8/1995 | Hutchison et al. | 250/435 |
| 5,471,063 A | 11/1995 | Hayes et al. | 250/436 |
| 5,504,335 A | 4/1996 | Maarschalkerweerd | 250/435 |
| 5,505,904 A | 4/1996 | Haidinger et al. | 422/24 |
| 5,529,689 A | 6/1996 | Korin | 210/232 |
| 5,532,549 A | 7/1996 | Duzyk et al. | 313/489 |
| 5,539,209 A | 7/1996 | Maarschalkerweerd | 250/436 |
| 5,540,848 A | 7/1996 | Engelhard | 210/748 |
| 5,547,635 A | 8/1996 | Duthie, Jr. | 422/24 |
| 5,560,958 A | 10/1996 | Duzyk et al. | 427/67 |
| 5,573,666 A | 11/1996 | Korin | 210/232 |
| 5,580,461 A | 12/1996 | Cairns et al. | 210/673 |
| 5,589,132 A | 12/1996 | Zippel | 422/24 |
| 5,590,390 A | 12/1996 | Maarschalkerweerd | 422/186.3 |
| 5,597,482 A | 1/1997 | Melyon | 210/209 |
| 5,611,918 A | 3/1997 | Markham | 210/87 |
| 5,612,001 A | 3/1997 | Matschke | 422/121 |
| 5,614,723 A | 3/1997 | Oppenländer et al. | 250/435 |
| 5,624,573 A | 4/1997 | Wiesmann | 210/748 |
| 5,626,768 A | 5/1997 | Ressler et al. | 210/748 |
| 5,628,895 A | 5/1997 | Zucholl | 210/85 |
| 5,655,483 A | 8/1997 | Lewis et al. | 119/720 |
| 5,660,719 A | 8/1997 | Kurtz et al. | 210/85 |
| 5,675,153 A | 10/1997 | Snowball | 250/438 |
| 5,707,594 A | 1/1998 | Austin | 422/186.3 |
| 5,744,094 A | 4/1998 | Castberg et al. | 422/24 |
| 5,753,106 A | 5/1998 | Schenck | 210/96.1 |
| 5,779,912 A | 7/1998 | Gonzalez-Martin et al. | 210/748 |
| 5,780,860 A | 7/1998 | Gadgil et al. | 250/432 R |
| 5,835,840 A | 11/1998 | Goswami | 422/186.3 |
| 5,846,437 A | 12/1998 | Whitby et al. | 210/748 |
| 5,874,740 A | 2/1999 | Ishiyama | 250/431 |
| 5,885,449 A | 3/1999 | Bergmann et al. | 210/198.1 |
| 5,911,910 A | 6/1999 | Becraft et al. | 252/188.28 |
| 5,925,320 A | 7/1999 | Jones | 422/121 |
| 5,933,702 A | 8/1999 | Goswami | 422/186.3 |
| 5,937,266 A | 8/1999 | Kadoya | 422/186.3 |
| 5,942,110 A | 8/1999 | Norris | 210/198.1 |
| 5,952,663 A | 9/1999 | Blatchley, III et al. | 250/435 |
| 5,958,336 A | 9/1999 | Duarte | 422/24 |
| 5,961,920 A | 10/1999 | Söremark | 422/24 |
| 5,997,812 A | 12/1999 | Burnham et al. | 422/24 |
| 6,013,917 A | 1/2000 | Ishiyama | 250/430 |
| 6,071,473 A | 6/2000 | Darwin | 422/20 |
| 6,083,387 A * | 7/2000 | LeBlanc et al. | 250/432 R |
| 6,090,296 A | 7/2000 | Oster | 210/748 |
| 6,120,691 A | 9/2000 | Mancil | 210/748 |
| RE36,896 E | 10/2000 | Maarschalkerweerd | |
| 6,126,841 A | 10/2000 | Whitby et al. | 210/748 |
| 6,129,893 A | 10/2000 | Bolton et al. | 422/23 |
| 6,149,343 A | 11/2000 | Lewis et al. | 405/127 |
| 6,150,663 A * | 11/2000 | Rosenthal | 250/435 |
| 6,183,652 B1 | 2/2001 | Crevasse et al. | 210/748 |
| 6,193,939 B1 | 2/2001 | Kozlowski | 422/186.3 |
| 6,202,384 B1 | 3/2001 | Kurth et al. | 53/141 |
| 6,217,834 B1 | 4/2001 | Hosein et al. | 422/186.3 |
| 6,231,820 B1 | 5/2001 | Wedekamp | 422/186.3 |
| 6,248,235 B1 | 6/2001 | Scott | 210/192 |
| 6,261,449 B1 | 7/2001 | Scott | 210/209 |
| 6,264,802 B1 | 7/2001 | Kamrukov et al. | 204/158.2 |
| 6,264,888 B1 | 7/2001 | Palestro et al. | 422/24 |
| 6,265,835 B1 | 7/2001 | Parra | 315/246 |
| 6,274,049 B1 | 8/2001 | Scott | 210/748 |
| 6,280,615 B1 * | 8/2001 | Phillips et al. | 250/436 |
| 6,299,844 B1 | 10/2001 | Tao et al. | 422/186 |
| 6,319,809 B1 | 11/2001 | Chang et al. | 438/597 |
| 6,328,937 B1 | 12/2001 | Glazman | 422/186.3 |
| 6,332,981 B1 | 12/2001 | Loyd | 210/198.1 |
| 6,358,478 B1 | 3/2002 | Söremark | 422/121 |
| 6,375,833 B1 | 4/2002 | Marston et al. | 210/85 |
| 6,398,971 B1 | 6/2002 | Butters et al. | 210/748 |
| 6,402,964 B1 | 6/2002 | Schmid | 210/748 |
| 6,403,030 B1 | 6/2002 | Horton, III | 422/24 |
| 6,404,111 B1 | 6/2002 | Kunkel | 313/24 |
| 6,419,821 B1 | 7/2002 | Gadgel et al. | 210/86 |
| 6,423,763 B1 | 7/2002 | Blasi | 523/161 |
| 6,436,299 B1 | 8/2002 | Baarman et al. | 210/748 |
| 6,447,720 B1 | 9/2002 | Horton, III et al. | 422/24 |
| 6,447,721 B1 | 9/2002 | Horton, III et al. | 422/24 |
| 6,454,937 B1 | 9/2002 | Horton et al. | 210/192 |
| 6,454,952 B1 | 9/2002 | Thorpe | 210/748 |
| 6,459,087 B1 | 10/2002 | Kaas | 250/372 |
| 6,461,520 B1 | 10/2002 | Engelhard et al. | 210/748 |
| 6,464,884 B1 | 10/2002 | Gadgil | 210/748 |
| 6,468,419 B1 | 10/2002 | Kunkel | 210/90 |
| 6,497,840 B1 | 12/2002 | Palestro et al. | 422/24 |
| 6,500,312 B2 | 12/2002 | Wedekamp | 204/157.15 |
| 6,500,346 B1 | 12/2002 | Taghipour et al. | 210/748 |
| 6,500,387 B1 | 12/2002 | Bigelow | 422/24 |
| 6,503,401 B1 | 1/2003 | Willis | 210/748 |
| 6,503,447 B1 | 1/2003 | Mondjian et al. | 422/4 |
| 6,534,001 B1 | 3/2003 | Michael et al. | 422/24 |
| 6,547,963 B1 | 4/2003 | Tsai | 210/232 |
| 6,565,757 B1 | 5/2003 | Wedkamp | 210/748 |
| 6,565,803 B1 | 5/2003 | Bolton et al. | 422/24 |
| 6,583,422 B2 | 6/2003 | Boehme | 250/432 R |
| RE38,173 E | 7/2003 | Ishiyama | |
| 6,568,489 B1 | 7/2003 | Morrow et al. | 422/186.3 |
| 6,589,323 B1 | 7/2003 | Korin | 96/223 |
| 6,589,489 B2 | 7/2003 | Morrow et al. | 422/186.3 |
| 6,589,490 B1 | 7/2003 | Parra | 422/186.3 |
| 6,599,487 B1 | 7/2003 | Luthra et al. | 422/186.3 |
| 6,602,425 B2 | 8/2003 | Gadgil et al. | 210/744 |
| 6,605,260 B1 | 8/2003 | Busted | 422/186.3 |
| 6,610,258 B1 | 8/2003 | Strobbel et al. | 422/186.3 |
| 2002/0033369 A1 | 3/2002 | Bender | |
| 2002/0043504 A1 | 4/2002 | Chen et al. | |
| 2002/0050479 A1 | 5/2002 | Scott | |
| 2002/0070177 A1 | 6/2002 | Kozlowski | |
| 2002/0081246 A1 | 6/2002 | Tsukada et al. | |
| 2002/0094298 A1 | 7/2002 | Monagan | |
| 2002/0098127 A1 | 7/2002 | Bollini | |
| 2002/0144955 A1 | 10/2002 | Barak et al. | |
| 2002/0170815 A1 | 11/2002 | Fuji | |
| 2002/0172627 A1 | 11/2002 | Aoyagi | |
| 2003/0010927 A1 | 1/2003 | Wedekamp | |
| 2003/0021721 A1 | 1/2003 | Hall | |
| 2003/0035750 A1 | 2/2003 | Neuberger | |
| 2003/0039576 A1 | 2/2003 | Hall | |
| 2003/0049809 A1 | 3/2003 | Kaiser et al. | |
| 2003/0064001 A1 | 4/2003 | Fries et al. | |
| 2003/0089670 A1 | 5/2003 | Saccomanno | |
| 2003/0099569 A1 | 5/2003 | Lentz et al. | |
| 2003/0127603 A1 | 7/2003 | Horowitz et al. | |
| 2003/0129105 A1 | 7/2003 | Boehme | |
| 2003/0147770 A1 | 8/2003 | Brown et al. | |
| 2003/0147783 A1 | 8/2003 | Taylor | |
| 2003/0150708 A1 | 8/2003 | Fink | |
| 2003/0155228 A1 | 8/2003 | Mills et al. | |
| 2003/0155524 A1 | 8/2003 | McDonald et al. | |

* cited by examiner

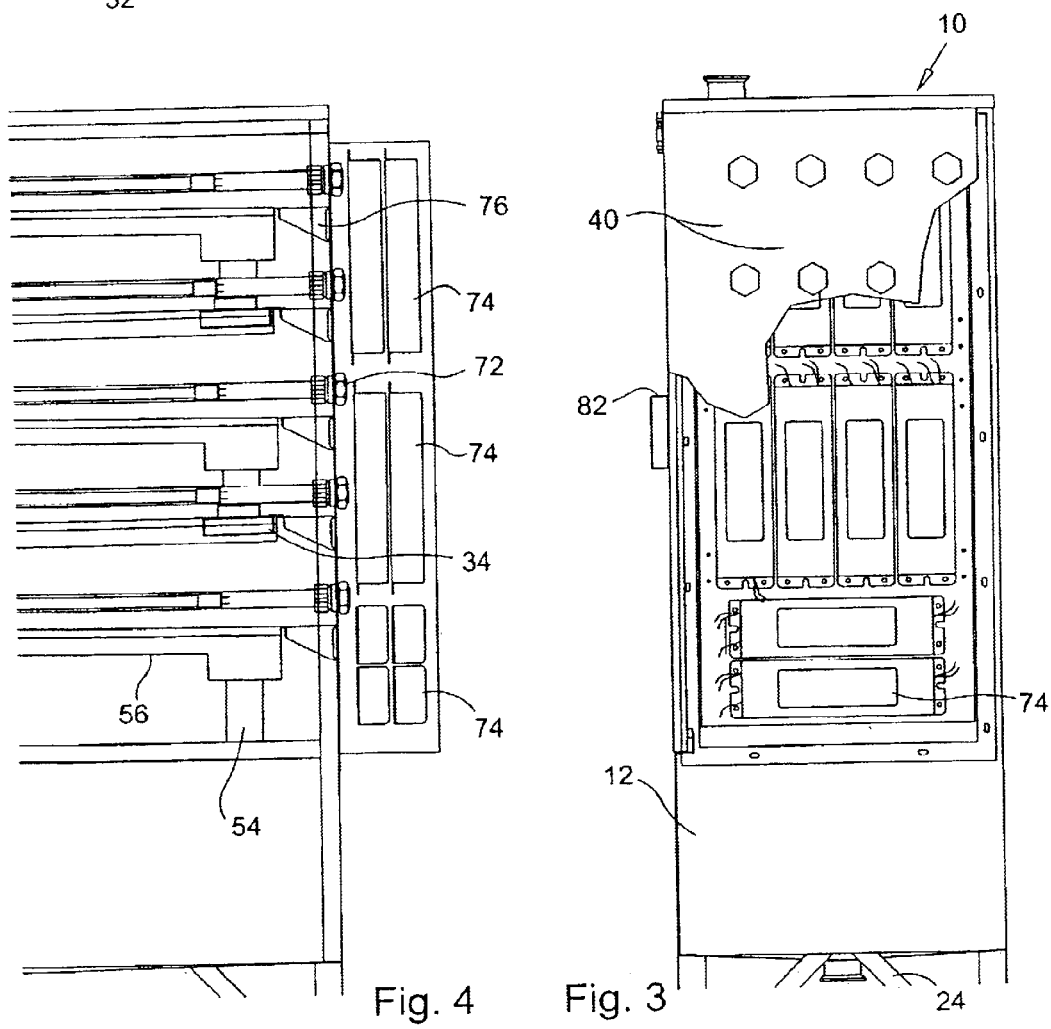

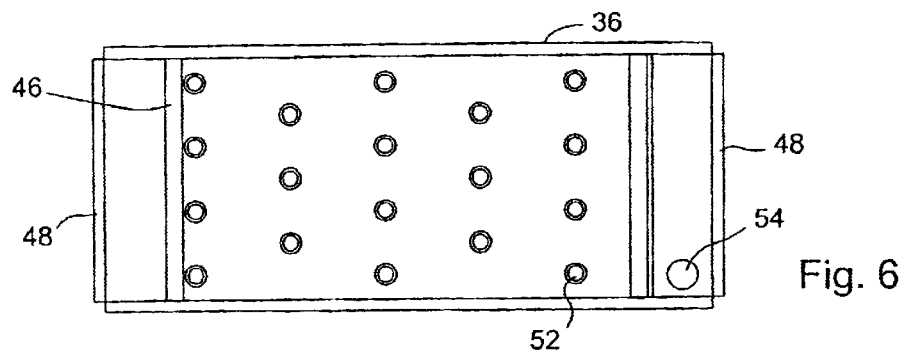
Fig. 6
Fig. 7
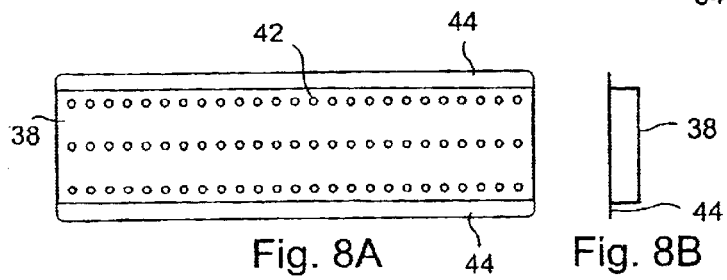
Fig. 8A   Fig. 8B   Fig. 9A
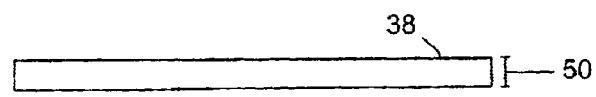 
Fig. 8C   Fig. 9B
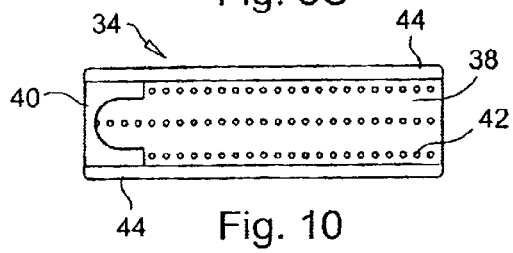
Fig. 10
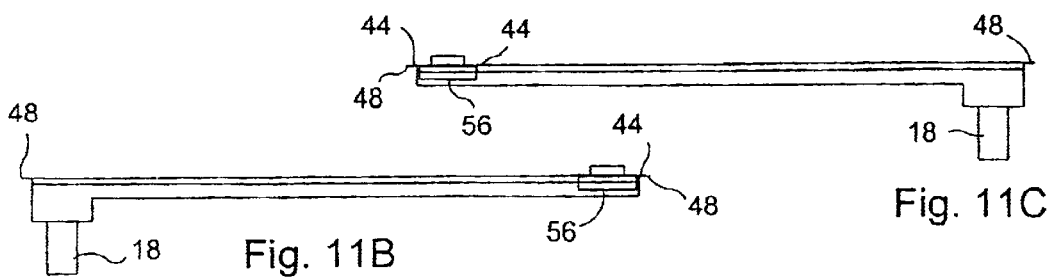
Fig. 11B   Fig. 11C

FOOD SANITIZING CABINET

BACKGROUND OF THE INVENTION

1. Field of the Invention

The present invention relates to sanitation of a liquid and more particularly pertains to compact, efficient devices used for irradiation of liquids such as those used in foods and food processing. The present invention also relates to liquids sanitized by such devices.

2. Description of Related Art

Food sanitation is a growing concern in the world. More and more aggressive disease causing agents are discovered every year. Moreover, an increasing number of people are made ill each year by eating contaminated foods. Also, the numbers of foods linked to food-caused illnesses continues to increase. Nonetheless, the desire for safer foods is higher than ever. In fact, state and federal jurisdictions are requiring that businesses use the most efficacious food safety and sanitation practices.

Efficient use of modern sanitation techniques decreases the cost of applying them. These savings, when passed to the consumer, mean the consumers spend less on the processed foods. Also, efficient sanitizing techniques can allow more food to be processed in a smaller amount of space. Thus smaller facilities may compete with larger ones, thereby increasing competition between processors and also lowering prices to consumers. In addition, facilities that use less-safe processing techniques may be easily retrofit to install an efficient apparatus. Also, the modularity of a new sanitizing apparatus makes it easy to manufacture and easy to replace parts for the apparatus.

Sanitizing radiation allows a highly controllable application of organism-killing radiation to foods and food additives. The use of sanitizing radiation in the food industry in general is well known in the prior art, and has been used in a variety of forms, including gamma ray radiation, ultraviolet (UV) light and infrared radiation.

For example, it is well known that the use of gamma radiation and UV radiation has been used in some countries for the sterilization of spices and animal feeds. However, over-use of ultraviolet radiation may cause undesirable chemical reactions with a food or food additive, which can cause the food or food additive to obtain undesirable flavors or textures. Also, various vitamins and proteins may be altered or destroyed through being subjected to too much radiation, reducing the food value of the treated product.

Traditional methods of irradiating liquid foods and food additives used an unnecessary amount of space in a food processing facility. They have long conveyors or hard-to-reach pipelines. For example, U.S. Pat. No. 6,150,663 to Rosenthal teaches a system incorporating a pair of stainless steel cones placed end-to-end and jacketed with steel to treat a liquid flowing through a pipeline. The entire system is linear in flow and an inefficient use of space. Moreover, in the prior art different systems are used for different processes. The lack of a modular system makes utilization the sanitizing radiation difficult to apply or manufacture on a large scale, or to retrofit into an existing system.

There is no system designed with modularity in mind, to suit different processes properly, or to provide easy replacement of component parts. There is no system wherein the radiation sources as well as the paths for the liquid to be sanitized are both optimized for radiation treatment and are highly modular in design. There is no system that treats liquid as a thin film, governed principally by its surface tension, thereby allowing sanitization of fluids even with a relatively high opacity. There is no system that is easy to assemble, clean, maintain and disassemble. There is no system using sanitizing radiation which is compact and enclosable, so high levels of the radiation may be used in a small amount of space and still be safe for operators. There is no system which takes advantage of the flowing characteristics of a liquid to form a cascade in a sanitization process, thereby reducing the length that another apparatus providing an equivalent amount of sterilizing radiation would have to take up.

SUMMARY OF THE INVENTION

The present invention is a compact, efficient, easy-to-maintain. enclosable apparatus for sanitizing a liquid flowing along a cascade within a cabinet body, having means for directing the liquid along a predetermined path within the cabinet body and means for subjecting the liquid to a sanitizing radiation for a predetermined time while flowing along the predetermined path, whereby the liquid is subject to suffciient sanitizing radiation for a predetermined level of sanitization. In one embodiment, the means for directing the liquid comprises a plurality of downward sloping irradiation, trays whereby liquid travels from one irradiation tray to another irradiation tray. Preferably, the irradiation trays have one or more elements adapted for increasing the turbulent circulation of the liquid, and the liquid is diffused before the liquid reaches an irradiation tray so that the liquid flows generally the width of the irradiation tray. The cabinet body includes an ingress and an egress.

In an alternative embodiment, each irradiation tray comprises a plurality of elements adapted for increasing circulation of the liquid. In another embodiment, the means for subjecting the liquid to a sanitizing radiation comprises one or more. irradiation assemblies in optical contact with the surface of the liquid. In yet another embodiment, the irradiation assembly comprises a UV light source and a UV light shield located between the UV light source and the liquid. In still another embodiment, the irradiation assembly further comprises a rigid reflector shield located between the UV light source and the UV light shield. In yet another embodiment, the reflector shield provides resistance to ease the attachment of the irradiation assembly to the cabinet body and strength to the irradiation assembly to resist damage during maintenance activity including hosing.

In another embodiment, the means for diffusing includes one or more diffusing trays, each diffusing tray including several voids through the bottom surface. In still another embodiment, the irradiation trays have one or more down pipes at a downstream position. The diffusing trays further may include a generally c-shaped splash guard piece, and the down pipe of an irradiation tray above the diffusing tray is in complementary contact with the splash guard. The diffusing tray and the irradiation tray may be easily removable.

In yet another embodiment, the egress includes a sloping bottom interior surface of the cabinet body toward a drain pipe in gravity flow connection with the sloping bottom. In still another embodiment, the amount of radiation exposure to the liquid is a function of the opacity of the liquid, the rate of low of the liquid, the intensity of the source of the sanitizing radiation, the distance between the sanitizing radiation and the liquid, the time the liquid spends under the sanitizing radiation.

In still another embodiment, the invention is an irradiation assembly for use in irradiating a liquid flowing in cascade within an enclosable cabinet, comprising a UV light source. a UV light shield located between the UV light source and the liquid and a rigid internal reflector shield located between the UV light source and the UV light shield. In yet another embodiment, the assembly has an endcap located on each end of the UV light shield for attachment of the assembly within the interior of the cabinet. The endcap may further include a rigid sheath having threads, located around the perimeter of the UV light shield, an endpiece having threads which are complementary to those on the sheath located on the exterior of the cabinet; and a compressive gasket, whereby engagement of the endpiece with the sheath generally seals the assembly to the interior of the cabinet.

In yet still another embodiment, the invention is a compact, efficient, easy-to-maintain enclosable cabinet for sanitizing a liquid having a cabinet body, a plurality of troughs directing the liquid along a predetermined path including a cascade within the cabinet body; and one or more sanitizing radiation sources for subjecting the liquid to a sanitizing radiation for a predetermined time while flowing along the predetermined path, whereby the liquid is subject to sufficient sanitizing radiation for a predetermined level of sanitization. At least one trough preferably is an irradiation tray oriented so the liquid flows from a first end to a second end with a down pipe located at the second end and a diffuser at the first end. The sanitizing radiation source is an array of UV light sources. Preferably, the sanitizing radiation source is at least two horizontal rows of four UV light sources. In still another embodiment, the apparatus is modular in design.

The invention also comprises a method for sanitizing a liquid within a compact, efficient, easy-to-maintain enclosable apparatus, comprising the steps of providing an ingress for the liquid into a cabinet body, directing the liquid along a plurality of troughs so that the liquid travels along a predetermined vertical and horizontal path within the cabinet body; and subjecting the liquid to one or more sanitizing radiation sources for a predetermined time while flowing along the predetermined path, whereby the liquid is subject to sufficient sanitizing radiation for a predetermined level of sanitization. In another embodiment, the method includes the step of providing an egress for the liquid after exposure to the sanitizing radiation.

It is an object of this invention to provide an apparatus designed with modularity in mind, to suit the processing of different foods or food additives, thereby making it economically beneficial to manufacture in assembly line fashion.

It is also an object of this invention to provide an apparatus in which the radiation sources as well as the paths for the liquid to be sanitized are optimized for radiation treatment and are highly modular in design.

It is also an object of this invention to provide a system for sanitizing a liquid that treats the liquid as a thin film, governed principally by its surface tension, thereby allowing sanitization of the liquid even having a relatively high opacity with regard to the sanitizing radiation.

It is also an object of this invention to provide a compact apparatus for sanitizing a liquid that is easy to assemble, clean, maintain and disassemble.

It is also an object of the invention to provide an apparatus using sanitizing radiation, which is compact and enclosable, so high levels of the radiation may be used in a small amount of space and still be safe for operators.

It is also an object of this invention to provide an apparatus which takes advantage of the flowing characteristics of a liquid to form a cascade in a sanitization process, thereby reducing the amount of mechanical parts or pumping action required.

It is also an object of the invention to reduce the horizontal length necessary to irradiate a liquid.

In accordance with these and other objects which will become apparent hereinafter, the instant invention will now be described with particular reference to the accompanying drawings.

In accordance with these and other objects which will become apparent hereinafter, the instant invention will now be described with particular reference to the accompanying drawings.

BRIEF DESCRIPTION OF THE DRAWINGS

FIG. 3 is a right side view of the invention.

FIG. 4 is a detail cut-away view of the front right side of the invention

FIG. 5a is a top view of the bottom portion of the cabinet of the invention.

FIG. 5b is a side view of the bottom portion of the cabinet of the invention.

FIG. 6 is a top view of an irradiation tray of the invention.

FIG. 7 is side view of an irradiation tray of the invention.

FIG. 8a is an top view of a diffuser tray of the invention.

FIG. 8b is an end view of a diffuser tray of the invention.

FIG. 8c is a side view of a diffuser splash guard of the invention.

FIG. 9a is a top view of a c-shaped splash guard of the invention.

FIG. 9b is a side view of a c-shaped splash guard of the invention.

FIG. 10 is a top view of diffuser including a splash guard.

FIG. 11b is a side view of a diffuser and right-running irradiation tray assembly.

FIG. 11c is a side view of a diffuser and left-running irradiation tray assembly.

DETAILED DESCRIPTION

Figure 1A:
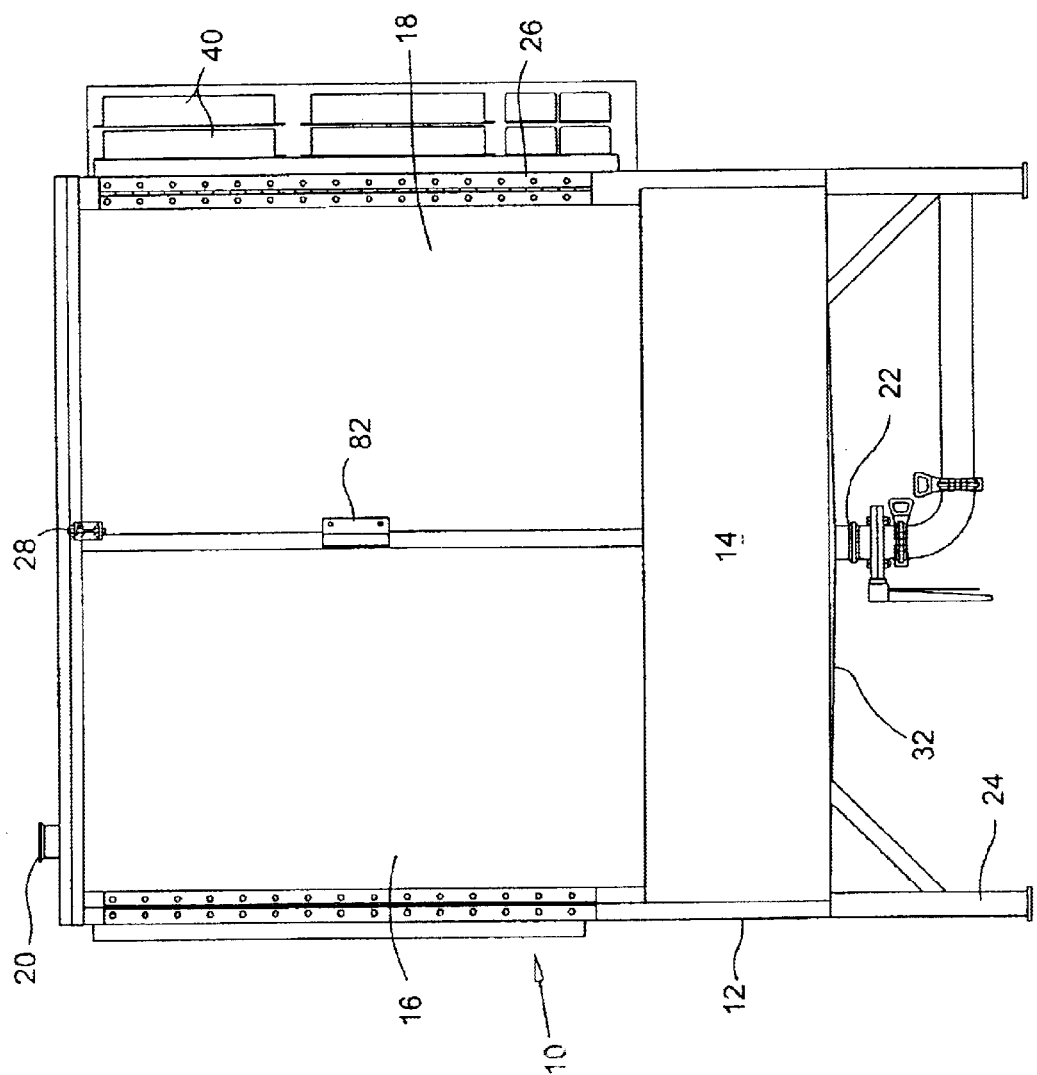
FIG. 1a is a front view of the preferred embodiment of the invention with the cabinet doors shut.
Figure 1B:
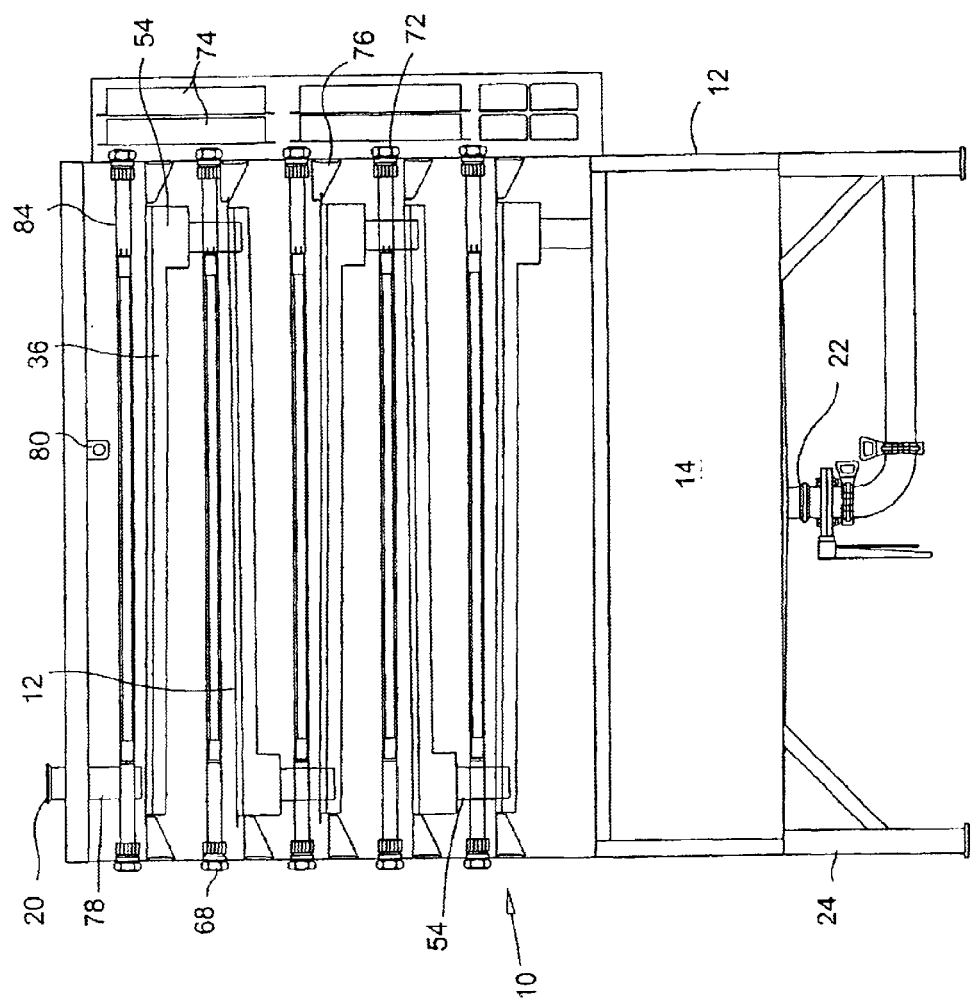
FIG. 1b is a front view of the preferred embodiment of the invention with the cabinet doors removed.

The present invention is a compact, efficient, easy-to-maintain enclosable apparatus for sanitizing a liquid, in a cascade, shown generally in FIGS. 1a and 1b as 10. FIG. 1a illustrates the exterior of the apparatus 10, showing the cabinet body 12 front side 14 with its doors 16, 18 shut. It is preferred that the doors 16, 18 swing open on hinges 26, and a handle 82 is used to open and shut the doors 16, 18. A latch 28 or other securing means prevents the doors 16, 18 from accidentally being opened. It is also preferred that the apparatus 10 has a sensor 80 as shown in FIG. 1b, to halt liquid flow and/or sanitizing radiation when the doors 16, 18 are opened.

The cabinet body 12 includes an ingress 20 for liquids to enter the cabinet body 12 located generally at the top of the cabinet body. An egress 22 for liquids after sanitation is located generally at the bottom of the apparatus 10. As shown in FIGS. 1*a,* 1*b* and 2, it is preferred that the apparatus stands in legs 24. It is also preferred that the bottom portion 32 of the cabinet body 12, shown in FIGS. 5*a* and 5*b,* is contoured so that liquid contacting the top surface 30 of the bottom portion 32 is directed generally toward the egress 22. However, other configurations are contemplated and may be preferred, depending upon the usage and placement of the apparatus 10 by the operator.

The interior configuration of the apparatus 10 is shown in FIGS. 1*b* and 4. As shown, within the apparatus 10 the liquid to be sanitized is diffused and then routed across radiation sources for sanitation in a cascade. In the preferred embodiment, the apparatus 10 includes a plurality of diffusers 34 located in fluid connection with irradiation trays 36. The preferred embodiment of the diffuser 34 and irradiation tray 36 are shown in detail in FIGS. 6–11. A diffuser 34 is illustrated in FIGS. 8–10, and comprise a diffuser tray, shown i,n FIGS. 8*a–*8*c* and a generally c-shaped splash guard 40, shown in FIGS. 9*a–*9*b.* It is preferred that the splash guard 40 is welded to the diffuser tray 38 to form diffuser 34, as shown in FIG. 10. However, other means for attachment for the splash guard are known in the art and may be used. The diffusers 34 have voids 42 to diffuse liquid within the apparatus 10 before it flows down into irradiation tray 36. The diffuser tray height 50, shown in FIG. 8*c,* as well as the shape, size and number of voids 42 may be optimized for dispersion of the liquid, and depend upon the volume of the liquid flowing as well as its thickness or viscosity. In the preferred embodiment, the diffuser 34 further comprises flanges 44 to allow the diffuser 34 to be held in place by a diffuser support 46 and a lip 48 located on the irradiation tray 36, as illustrated in FIGS. 6 and 11. The diffuser 34 is located so that liquid within the apparatus 10 is diffused by the diffuser 42 and flows through the voids 42 into an irradiation tray 34 below it, for processing and/or sanitization.

Figure 11A:
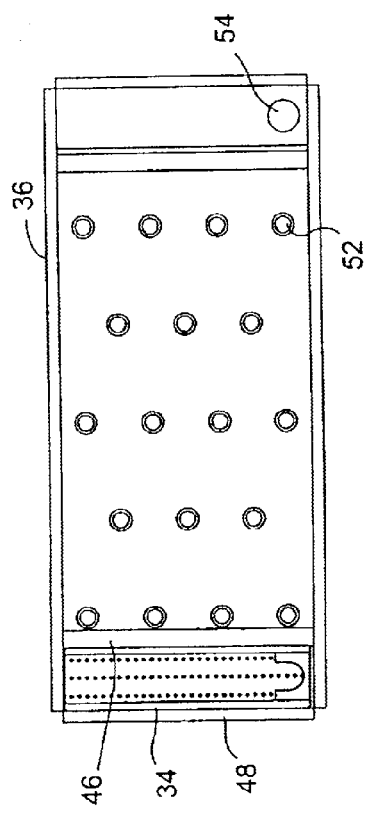
FIG. 11a is a top view of a diffuser and irradiation tray assembly.
Figure 12:
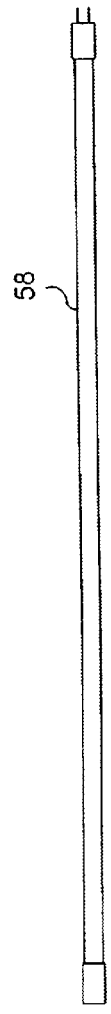
FIG. 12 is a side view of a sanitizing radiation source the invention.
Figure 13:
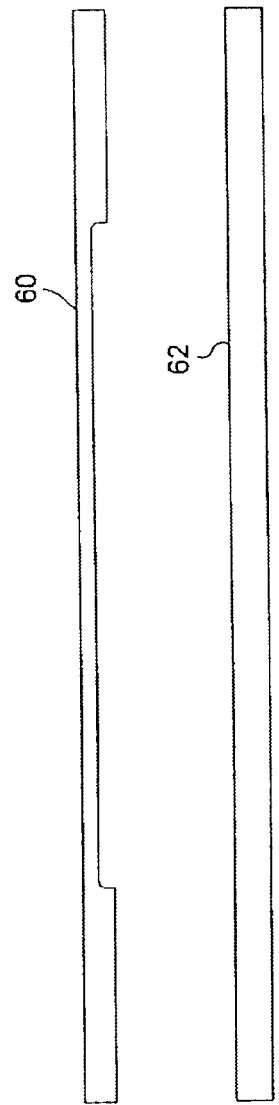
FIG. 13 is a side view of a reflecting tube of the invention.
Figure 14:
FIG. 14 is a side view of a shield of the invention.

The irradiation tray 36 is illustrated in FIGS. 6–7. It includes elements 52 to optimize the turbulent flow of the liquid being sanitized. It also comprises a place for holding a diffuser 34 on one side, and a place for outflow of the liquid, such as a down pipe 54, on the other side. Preferably, there is a temporary fill area 56 which allows liquid to collect above the down pipe 54 after passing over the elements 52, thereby reducing the risk of splashing within the apparatus 10. In the preferred embodiment, the down pipe 54 fits complementarily with the recess of the splash guard 40 of an irradiation tray 36 below it, as shown generally in FIGS. 1*b* and 4. Thus, the irradiation trays 36 are both right-flowing and left-flowing in design. A right-flowing irradiation tray 36 with diffuser 42 is shown in FIGS. 11*a* and 11*b,* and a left-flowing irradiation tray 36 with diffuser 42 is shown in FIG. 11*c.*

Over each irradiation tray 36 is at least one sanitizing radiation source. In the preferred embodiment, four (4) sanitizing radiation sources are used for each irradiation tray 36. The preferred embodiment of a radiation source is a bulb and assembly as illustrated in FIGS. 12–15. The bulb is preferred to be a low-pressure mercury vapor UV light 58, capable of emitting UV light of approximately 254 nm. It is also preferred that the UV light have its electrical connectors 70 on one side rather than both sides. While the right side is illustrated and discussed, they may alternatively be found on the left side. It is also preferred that the bulbs are made from shatterproof glass.

Preferably, around the light 58 is a reflector tube 60. The tube 60 has a highly reflective interior surface, so the radiation from the radiation source 58 is used more efficiently onto the liquid being sanitized by the apparatus 10. Also, it is preferred that the tube 60 be rigid to help in securing the connection of the sanitizing radiation source to the interior of the cabinet body 12. The reflecting tube 60 is positioned so that radiation emitted away from the liquid is redirected generally toward the liquid. It is also preferred that the reflecting tube 60 is of a length designed so that radiation to the liquid from the sanitizing radiation source is not obstructed. The reflecting tube is generally cylindrical; however, the interior geometry may be altered to optimize reflection of the sanitizing radiation onto the liquid.

The preferred material for the tube 60 is aluminum; however, other metals may be used, or a reflective coating on the interior surface of a rigid, generally cylindrical piece. Around the tube 60 is preferably a shield 62, to shield the liquid from any material that may possibly fall into the liquid if the radiation source breaks. Preferably, the shield 62 is a transparent, generally flexible cylinder made from fluorocarbon. However, other materials may be used.

Figure 15:
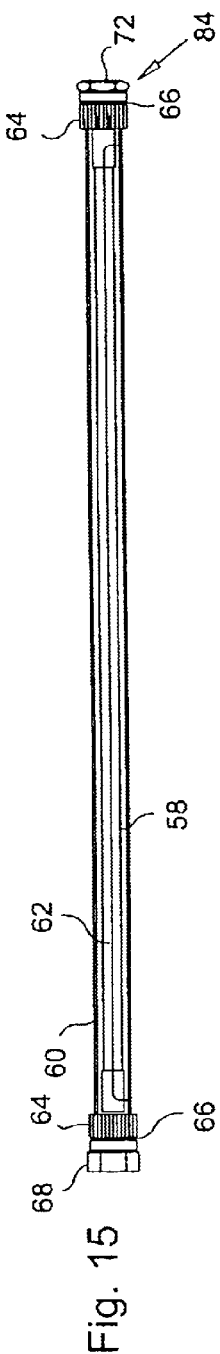
FIG. 15 is a side view of a sanitizing radiation assembly of the invention.

In the preferred embodiment, as shown in FIG. 15, on each end of the shield 62 is an endcap fitting 64. Each endcap fitting 64 is generally cylindrical and allows each end of the shield 62 to fit at least partway within it. Around each endcap fitting 64 is a means for forming a compressive seal, such as a gasket 66. On the far end of each endcap fitting 64 is an endcap. A closed endcap 68 is preferred for the end of the UV light 58 that has no electrical connectors 70 to protect the radiation sources and to reduce radiation escaping from the apparatus 10. An open endcap 72 is preferred for the end of the UV light 58 that has electrical connectors 70 to facilitate access to wiring (not shown) of the UV light 58, for example to elements such as ballast circuits 74 attached to the outer surface of the cabinet body 12. Ballast circuits 74 attached to the apparatus 10 are illustrated in FIGS. 1*a,* 1*b,* 3 and 4. In the preferred embodiment, the endcap fittings 64 and the endcaps 66, 72 have complementary threads, so that screwing the endcaps 68, 72 onto the endcap fittings 64 compresses the compressive seal 66. The UV light assembly 84, including endcaps 68, 72 is shown in FIG. 15.

UV light assemblies 84 are fit onto the cabinet body 12 as shown in FIGS. 1*b* and 4. Compression of the gasket 66 around the endcap fitting 64 helps seal the sanitizing radiation source into the cabinet 12. The rigid tube 60 helps provide resistance for screwing the endcaps 68, 72 onto the endcap fittings 64, to form the compressive seal. The rigid tube 60 also forms a support for the shield 62 so that the shield 62 goes not contact the UV light 58 during maintenance, thereby causing the UV light 58 to break.

As shown in FIG. 1*b,* the irradiation trays 36 are placed within the cabinet body 12, on support brackets 76. The support brackets 76 are preferably offset so that fluid within an irradiation tray 36 flows downward towards the down pipe 54. It is preferred that the radiation trays 36 are approximately one quarter inch offset from level to facilitate liquid flow.

Alternatively, the brackets 76 may hold the irradiation trays 36 level, while the irradiation trays themselves have a downhill gradient toward the down pipe 54. The irradiation trays 36 within the cabinet body 12 are aligned with right-flowing irradiation trays 36 alternating with left-flowing irradiation trays 36, as shown generally in FIG. 1*b* to form a cascade. Preferably, the first irradiation tray 36 in the cascade is fitted so the splash guard 40 of the diffuser 34 is placed under the ingress 20. The final irradiation tray 36 in the cascade permits the fluid to pass from the down pipe 54 to the egress 22.

Figure 2:
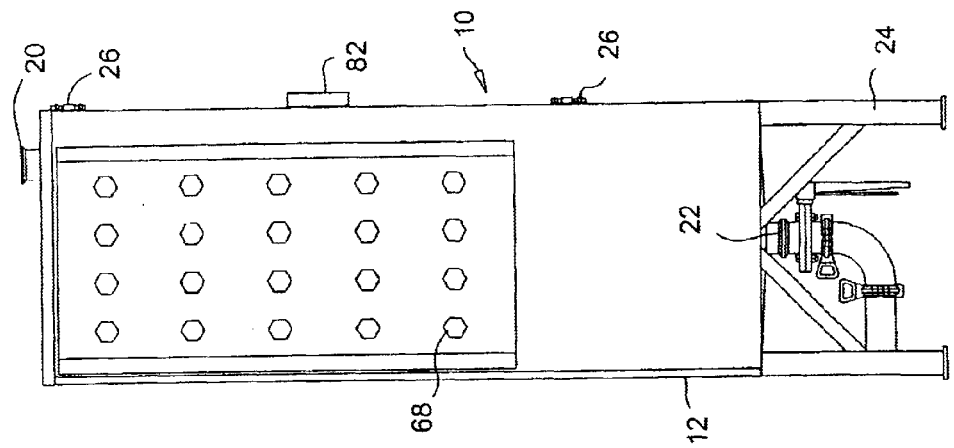
FIG. 2 is a left side view of the invention.

In the preferred embodiment, as shown in FIG. 1b and 2, the apparatus has five (5) alternating irradiation trays 36. Each irradiation tray 36 is irradiated by four (4) radiation sources in radiation assemblies 84. The assemblies 84 are approximately four (4) inches above the flowing liquid.

As shown in FIGS. 3 and 4, it is preferred that ballast circuits 74 for the radiation sources, when needed, are attached to the outside of the cabinet body 12. It is preferred to have them on one side, closest to the electrical connectors 70 of the radiation sources.

Liquid is sanitized by the apparatus 10 as follows. Liquid enters the cabinet body 12 through the ingress 20 into a first irradiation tray 36. The ingress 20 preferably includes an ingress pipe 78 which fits complementarily to a splash guard 40 on the first diffuser 34 on the first irradiation tray 36. The liquid is diffused by a diffuser 34, and flows down the irradiation tray 36. The liquid is roiled by elements 52 on the irradiation tray 36, thereby insuring sanitizing radiation through the liquid. As the liquid flows along the irradiation trays 36, it is subjected to sanitizing radiation from above, preferably using low-pressure mercury UV light sources. A generally cylindrical reflector tube 60 preferably focuses the radiation on the liquid, and a shield 62 preferably protects the liquid and the interior of the apparatus from materials if the light source were to break. The liquid flows down to a down pipe 54, complementarily fit into a splash guard 40 of an irradiation tray facing in the opposite direction. The liquid continues to flow down this irradiation tray 36 to successive irradiation trays 36 in cascade fashion, until the liquid has sufficiently been sanitized by the irradiation assemblies 84. The amount of radiation exposure to the liquid is optimized as, a function of the opacity of the liquid, the rate of flow of the liquid, the intensity of the source of the sanitizing radiation, the distance between the sanitizing radiation and the liquid, the time the liquid spends under the sanitizing radiation. In the preferred embodiment, the liquid spends approximately one to 1.5 seconds per irradiation tray 36. It is preferred that the liquid be exposed to 40 mW-seconds of sanitizing radiation. The liquid then flows from the last irradiation tray 36 to an egress 22 in the cabinet body 12.

The cabinet body 12 and the components are easy to maintain. IT is preferred that the elements touching the liquid and the cabinet body, be made of an easy to maintain food sanitary material, such as stainless steel. As described, the diffusers 34 and the irradiation trays 36 are easily removable from the cabinet body. Also, the sanitizing radiation sources such as the UV lights 58 as described in the preferred embodiment are easy to replace, simply by removing one or more of the endcaps 68, 72 to the approximate assembly 84 and removing the necessary radiation source. Furthermore, the wiring of the radiation sources is easy to access, since the open endcaps 72 allow access to the wiring, even when the apparatus 10 is in operation.

In an alternative embodiment, the apparatus includes a supply pump, flow meter and a control valve, such as a butterfly valve in place upstream from the ingress 20. In another alternative embodiment, a discharge pump, control valve and flow meter are in place down stream from the egress 22, as shown generally in FIGS. 1a, 1b and 2. The cabinet body 12 may also have overflow openings and controls within the cabinet body above the egress 22.

The instant invention has been shown and described herein in what is considered to be the most practical and preferred embodiment. It is recognized, however, that departures may be made therefrom within the scope of the invention and that obvious modifications will occur to a person skilled in the art.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A compact, efficient, easy-to-maintain enclosable apparatus for sanitizing a liquid flowing along a cascade, comprising:
   a cabinet body;
   means for directing the liquid along a predetermined path within the cabinet body; and
   means for subjecting the liquid to a sanitizing radiation for a predetermined time while flowing along the predetermined path;
   wherein the means for directing the liquid comprises a plurality of downward sloping irradiation trays whereby liquid travels from one irradiation tray to another irradiation tray;
   whereby the liquid is subject to sufficient sanitizing radiation for a predetermined level of sanitization.

2. The apparatus of claim 1, wherein the downward sloping irradiation trays each comprise offset support brackets whereby liquid travels from one irradiation tray to another irradiation tray.

3. The apparatus of claim 1, wherein one or more irradiation trays comprises one or more elements adapted for increasing the turbulent circulation of the liquid.

4. The apparatus of claim 1, wherein the means for directing liquid further comprises a means for diffusing the liquid before the liquid reaches an irradiation tray so that the liquid flows generally the width of the irradiation tray.

5. The apparatus of claim 1, further comprising:
   an ingress for accepting input of the liquid into the interior of the apparatus located generally at the top portion of the apparatus; and
   an egress for discharging the liquid after sanitization located generally at the bottom portion of the apparatus.

6. The apparatus of claim 1, wherein each irradiation tray comprises a plurality of elements adapted for increasing circulation of the liquid.

7. The apparatus of claim 1, wherein the means for subjecting the liquid to a sanitizing radiation comprises one or more irradiation assemblies in optical contact with the surface of the liquid.

8. The apparatus of claim 7, wherein an irradiation assembly comprises:
   a UV light source; and
   a UV light shield located between the UV light source and the liquid.

9. The apparatus of claim 8, wherein the irradiation assembly further comprises a rigid reflector shield located between the UV light source and the UV light shield.

10. The apparatus of claim 9, wherein the reflector shield provides resistance to ease the attachment of the irradiation assembly to the cabinet body and strength to the irradiation assembly to resist damage during maintenance activity including hosing.

11. The apparatus of claim 4, wherein the means for diffusing comprises:
   one or more diffusing trays, each diffusing tray including a plurality of voids through the bottom surface of the diffusing tray for diffusing the liquid.

12. The apparatus of claim 1, wherein one or more irradiation trays further comprises one or more down pipes at a downstream position on the irradiation tray.

13. The apparatus of claim 11, wherein one or more diffusing trays further includes a generally c-shaped splash guard piece whereby splash of liquid contacting the diffusing tray is reduced.

14. The apparatus of claim 11, wherein one or more diffusing trays further includes a generally c-shaped splash guard piece wherein splash of liquid contacting the diffusing tray is reduced, and wherein the down pipe is in complementary contact with the splash guard.

15. The apparatus of claim 11, wherein the diffusing tray is easily removable.

16. The apparatus of claim 1, wherein the irradiation tray is easily removable.

17. The apparatus of claim 5, wherein the egress includes a sloping bottom interior surface of the cabinet body toward a hole in gravity flow connection with the sloping bottom.

18. The apparatus of claim 1, wherein the amount of radiation exposure to the liquid is optimized as a function of the opacity of the liquid, the rate of flow of the liquid, the intensity of the source of the sanitizing radiation, the distance between the sanitizing radiation and the liquid and the time the liquid spends under the sanitizing radiation.

19. A modular sanitizing radiation source, comprising:
   an irradiation assembly for use in irradiating a liquid flowing in a cascade within an enclosable cabinet, comprising:
      a UV light source;
      a UV light shield located between the UV light source and the liquid; and
      a rigid internal reflector shield located between the UV light source and the UV light shield.

20. The assembly of claim 19, further comprising an endcap fitting assembly located on each end of the UV light shield for attachment of the assembly within the interior of the cabinet.

21. The assembly of claim 20, wherein the endcap fitting assembly comprises:
   a rigid endcap fitting having threads, located around the perimeter of the UV light shield;
   an endcap having threads which are complementary to those on the sheath located on the exterior of the cabinet; and
   a compressive gasket, whereby engagement of the endcap with the endcap fitting generally seals the endcap fitting assembly to the interior of the cabinet.

22. A compact, efficient, easy-to-maintain enclosable cabinet for sanitizing a liquid, comprising:
   a cabinet body;
   a plurality of troughs directing the liquid along a predetermined path including a cascade between trays within the cabinet body; and
   one or more sanitizing radiation sources for subjecting the liquid to a sanitizing radiation for a predetermined time while flowing along the predetermined path;
   whereby the liquid is subject to sufficient sanitizing radiation for a predetermined level of sanitization.

23. The cabinet of claim 22, wherein at least one trough comprises:
   an irradiation tray oriented so the liquid flows from a first end to a second end;
   a down pipe located at the second end;
   a diffuser at the first end.

24. The cabinet of claim 22, wherein the sanitizing radiation source comprises an array of UV light sources.

25. The cabinet of claim 23, therein the sanitizing radiation source further comprises at least two horizontal rows of four UV light sources.

26. The cabinet of claim 22, wherein the apparatus includes modules of sanitizing radiation sources comprising:
   an irradiation assembly, comprising:
      a UV light source;
      a UV light shield located between the UV light source and the liquid; and
      a rigid internal reflector shield located between the UV light source and the UV light shield.

27. A method for sanitizing a liquid within a compact, efficient, easy-to-maintain enclosable apparatus, comprising the steps of:
   providing an ingress for the liquid into a cabinet body;
   directing the liquid along a plurality of generally horizontal troughs so that the liquid travels along a predetermined vertical and horizontal path within the cabinet body; and
   subjecting the liquid to one or more sanitizing radiation sources for a predetermined time while flowing along the predetermined path,
   whereby the liquid is subject to sufficient sanitizing radiation for a predetermined level of sanitization.

28. The method of claim 27, further comprising the step of providing an egress for the liquid after exposure to the sanitizing radiation.

* * * * *

UNITED STATES PATENT AND TRADEMARK OFFICE
CERTIFICATE OF CORRECTION

| | | |
|---|---|---|
| PATENT NO. | : 6,784,440 B2 | Page 1 of 1 |
| APPLICATION NO. | : 10/206498 | |
| DATED | : August 31, 2004 | |
| INVENTOR(S) | : Ronald G. Fink, Walter Ellis and Charles Pearsall | |

It is certified that error appears in the above-identified patent and that said Letters Patent is hereby corrected as shown below:

The third Inventor's name should be changed from "Bearsall" to --PEARSALL--.

Signed and Sealed this

Eleventh Day of December, 2007

JON W. DUDAS
*Director of the United States Patent and Trademark Office*